United States Patent
Auner et al.

(10) Patent No.: US 10,005,798 B2
(45) Date of Patent: Jun. 26, 2018

(54) PLASMA-ASSISTED ORGANOFUNCTIONALIZATION OF SILICON TETRAHALIDES OR ORGANOHALOSILANES

(75) Inventors: Norbert Auner, Glashuetten (DE); Christian Bauch, Usingen (DE); Rumen Deltschew, Leipzig (DE); Gerd Lippold, Markkleeberg (DE); Seyed-Javad Mohsseni-Ala, Bitterfeld-Wolfen (DE)

(73) Assignee: Nagarjuna Fertilizers and Chemicals Limited, Hyderabad, Telangana (IN)

(*) Notice: Subject to any disclaimer, the term of this patent is extended or adjusted under 35 U.S.C. 154(b) by 936 days.

(21) Appl. No.: 12/681,697

(22) PCT Filed: Mar. 31, 2008

(86) PCT No.: PCT/EP2008/002551
§ 371 (c)(1),
(2), (4) Date: Sep. 8, 2010

(87) PCT Pub. No.: WO2008/119540
PCT Pub. Date: Oct. 9, 2008

(65) Prior Publication Data
US 2011/0132744 A1 Jun. 9, 2011

(30) Foreign Application Priority Data
Mar. 30, 2007 (DE) .......... 10 2007 015 749

(51) Int. Cl.
C07F 7/12 (2006.01)
B01J 19/08 (2006.01)
C07F 7/08 (2006.01)

(52) U.S. Cl.
CPC .......... *C07F 7/122* (2013.01); *B01J 19/08* (2013.01); *C07F 7/0896* (2013.01)

(58) Field of Classification Search
CPC .......... C07F 7/122; C07F 7/0896; H05H 2001/4607; H05H 2001/4615; H05H 2001/4622; H05H 2001/4645; H05H 2001/4652; H05H 2001/466; H05H 2001/4667; H05H 2001/4675; H05H 2001/4682; B01J 19/08
USPC .......... 204/157.64, 157.74, 157.45, 157.94
See application file for complete search history.

(56) References Cited

U.S. PATENT DOCUMENTS

| | | | | |
|---|---|---|---|---|
| 2,403,370 A * | 7/1946 | Hurd | ................. | C07F 7/122 556/478 |
| 2,405,019 A * | 7/1946 | Dalin | ................. | C07F 7/122 204/157.74 |
| 2,796,397 A * | 6/1957 | Clasen | ................. | 422/186.12 |
| 2,899,371 A * | 8/1959 | Akerlof | ................. | 422/186.04 |
| 3,049,488 A * | 8/1962 | Bloom et al. | ................. | 422/186.29 |
| 3,444,061 A * | 5/1969 | Hellund | ................. | 422/186.04 |
| 3,450,617 A * | 6/1969 | Hellund | ................. | 422/186.04 |
| 3,642,596 A * | 2/1972 | Takamizawa et al. | ................. | 204/157.74 |
| 3,853,726 A * | 12/1974 | Vainshien et al. | ................. | 204/157.74 |
| 3,875,068 A * | 4/1975 | Mitzel | ................. | B01J 19/126 422/186.05 |
| 4,610,757 A | 9/1986 | Khoe et al. | | |
| 4,690,830 A | 9/1987 | Dickson et al. | | |
| 5,478,453 A | 12/1995 | Bernard et al. | | |
| 5,505,913 A * | 4/1996 | Bernard et al. | ................. | 422/186.04 |
| 5,560,890 A * | 10/1996 | Berman et al. | ................. | 422/186.04 |
| 5,750,823 A * | 5/1998 | Wofford | ................. | B01J 19/126 423/210 |
| 6,156,163 A * | 12/2000 | Langlois et al. | ................. | 204/157.94 |
| 7,309,471 B2 * | 12/2007 | Benje et al. | ................. | 422/186.1 |
| 2001/0055672 A1 * | 12/2001 | Todd | ................. | 428/212 |
| 2003/0091482 A1 * | 5/2003 | Weiler | ................. | H01J 37/32082 422/186 |

FOREIGN PATENT DOCUMENTS

| | | | |
|---|---|---|---|
| CN | 1237272 A | | 12/1999 |
| CN | 1402754 A | | 3/2003 |
| CN | 1807238 A | * | 7/2006 |
| DE | 230790 A | * | 12/1985 |
| DE | 3941997 C1 | | 1/1991 |
| DE | 60019691 T2 | | 3/2006 |
| DE | 102007007874 A1 | * | 8/2008 |
| EP | 0233613 A2 | | 8/1987 |
| EP | 0616260 A2 | | 9/1994 |
| GB | 741067 A | * | 11/1955 |
| SU | 282321 A | * | 7/1969 |
| WO | 1990/012754 A1 | | 11/1990 |
| WO | 2004/010454 A2 | | 2/2004 |

OTHER PUBLICATIONS

Chernyshev et al, "Gas-phase reaction of hexachlorodisilane with vinyl chloride and allyl chloride," Zhurnal Obschchei Khimii, vol. 66, No. 9, pp. 1484-1487, 1996 (English-language abstract provided).*
Chernyshev et al, "Reaction of Hexachlorodisilane with Trichloroethynylsilane and 2-Propynyl Chloride in the Gas Phase," Russian J. of General Chemistry, vol. 67, No. 7, 1997, pp. 1043-1046.*
SU 282321 A(Beta-alkenylsilanes) (English-language abstract provided).*

(Continued)

*Primary Examiner* — Ibrahime A Abraham
*Assistant Examiner* — Colleen M Raphael
(74) *Attorney, Agent, or Firm* — Harness, Dickey & Pierce, PLC

(57) ABSTRACT

The invention relates to a method for the plasma-assisted synthesis of organohalosilanes in which organohalosilanes of the general empirical formula $R^1{}_m R^2{}_o SiX_{4-p}$ (X=F, Cl, Br or I; p=1-4; p=m+o; m=1-4; o=0-3; $R^1$, $R^2$=alkyl, alkenyl, alkinyl, aryl) and/or carbosilanes of the general empirical formula $R^3{}_q SiX_{3-q} CH_2 SiR^4{}_r X_{3-r}$ (X=F, Cl, Br or I; q=0-3; r=0-3; $R^3$, $R^4$=alkyl, alkenyl, alkinyl, aryl) are formed by activating a plasma in a mixture of one or more volatile organic compounds from the group of alkanes, alkenes, alkines and aromates with $SiX_4$ and/or organohalosilanes $R_n SiX_{4-n}$ (X=F, Cl, Br oder I; n=1-4; R=alkyl, alkenyl, alkinyl, aryl).

19 Claims, No Drawings

(56) References Cited

OTHER PUBLICATIONS

Fritz et al, "Zur Bildung von Carbosilanen aus Methylsilanen," Zeitschrift für anorganische und allgemeine Chemie, vol. 460, Issue 1, pp. 115-143 (1980).*

Translation of Fritz et al, "Zur Bildung von Carbosilanen aus Methylsilanen," Zeitschrift für anorganische and allgemeine Chemie, vol. 460, Issue 1, pp. 115-143 (1980).*

* cited by examiner

PLASMA-ASSISTED ORGANOFUNCTIONALIZATION OF SILICON TETRAHALIDES OR ORGANOHALOSILANES

The present invention relates to a method for the plasma-assisted synthesis of organohalosilanes.

The state of the art is characterized in that dimethyldichlorosilane is obtained by the process known as the Müller-Rochow process from silicon and methyl chloride (gas) at 270-350° C. This process requires high-quality metallurgical silicon, which must further be admixed with catalysts (Cu) and precise amounts of promoters (various metals in small amounts). A disadvantage is the necessity of operating with relatively expensive metallurgical silicon and with expensive and toxic (carcinogenic) methyl chloride. In addition to the desired $Me_2SiCl_2$, fluctuating amounts of other silanes such as $MeSiCl_3$, $Me_3SiCl$, $Me_4Si$ and $SiCl_4$, and also higher-boiling oligosilanes, are also produced.

Solar cells comprising monocrystalline silicon possess a high efficiency, but are expensive to produce. Layers of amorphous silicon (a-Si) are more cost-effective, but for using a-Si it is advantageous to incorporate, into a hydrogenated amorphous silicon layer (a-Si:H), carbon (a-SiC$_x$:H), since this considerably enlarges the effective wavelength range of the sunlight.

a-SiC$_x$:H is generally obtained by chemical deposition from the gas phase (e.g., plasma-CVD) of gas mixtures composed of silane, hydrocarbons and hydrogen. In accordance with a process of this kind, however, the elements Si, C and H are deposited in a way which cannot be controlled with sufficient exactitude, and so unwanted chemical bonds may be formed that lower the efficiency. In order to avoid this effect, alkylsilanes rather than gas mixtures are used for producing a-SiC$_x$:H layers. Given that methylsilane, both in thermal deposition and in plasma deposition, leads to layers having a relatively low Si content or high C content and hence to a high electrical resistance, relatively silyl-rich compounds are used in accordance with the state of the art, such as, for example, bis(silyl)methane, $H_3SiCH_2SiH_3$ (cf. U.S. Pat. No. 4,690,830, EP-A-0233613). In accordance with the state of the art, this compound is prepared by reaction of chloroform with trichlorosilane (HSiCl$_3$) in the presence of an amine to give $H_2C(SiCl_3)_2$, which is reduced with lithium aluminum hydride (LiAlH$_4$) to bis(silyl)methane. Another preparation pathway starts from a reaction of dibromomethane with KSiH$_3$ [cf. Z. Naturforsch. 41b, pp. 1527-1534 (1986)]. DE 3941997 C1 reports on a three-stage synthesis.

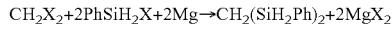

$CH_2X_2+2PhSiH_2X+2Mg \rightarrow CH_2(SiH_2Ph)_2+2MgX_2$

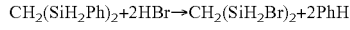

$CH_2(SiH_2Ph)_2+2HBr \rightarrow CH_2(SiH_2Br)_2+2PhH$

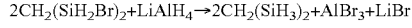

$2CH_2(SiH_2Br)_2+LiAlH_4 \rightarrow 2CH_2(SiH_3)_2+AlBr_3+LiBr$

Further suitable starting compounds for preparing disilylmethane are perhalogenated bis(silyl)methanes of the type $(X_3Si)_2CH_2$, where X most advantageously is chlorine. To date, however, there is no known synthesis for constructing $(Cl_3Si)_2CH_2$ from the easily obtainable and hence cost-effective building blocks represented by silicon tetrachloride and methane.

The invention is based on the object of providing a particularly simple and cost-effective method for the plasma-assisted synthesis of organohalosilanes.

This object is achieved in accordance with the invention by means of a method which is characterized in that a plasma is ignited in a mixture of one or more volatile organic compounds from the group consisting of alkanes, alkenes, alkynes and aromatics with $SiX_4$ and/or organohalosilanes $R_nSiX_{4-n}$ (X=F, Cl, Br or I; n=1-4; R=alkyl, alkenyl, alkynyl, aryl) to form organohalosilanes of the general empirical formula $R^1_m R^2_o SiX_{4-p}$ (X=F, Cl, Br or I; p=1-4; p=m+o; m=1-4; o=0-3; $R^1$, $R^2$=alkyl, alkenyl, alkynyl, aryl) and/or carbosilanes of the general empirical formula $R^3_q SiX_{3-q} CH_2 SiR^4_r X_{3-r}$ (X=F, Cl, Br or I; q=0-3; r=0-3; $R^3$, $R^4$=alkyl, alkenyl, alkynyl, aryl).

Developments of the method of the invention are described in the dependent claims. Thus one development is that wherein the reactant mixture is brought to reaction by use of a nonisothermal plasma. Further, the reactant mixture is brought to reaction preferably under reduced pressure.

The reactant mixture is passed advantageously through at least one plasma reaction zone. Further, it is passed preferably through a plurality of reaction zones and rest zones which follow one another alternately.

The reactant mixture is preferably reacted in a plasma reactor under a pressure of 0.1 to 100 hPa, preferably of 1.0 to 10.0 hPa. It is reacted advantageously at reaction temperatures of −80° C. to +400° C., preferably of 0° C. to 250° C.

To implement the plasma reactions, alternating electromagnetic fields, especially, are coupled in, preferably in the 1.0 MHz to 2.45 GHz range.

In further development, the reaction products are obtained in a collecting vessel downstream of the plasma reactor by low-temperature condensation of approximately −80° C. The organohalosilanes are preferably obtained from a distillation vessel in a distillation column by distillation and are collected in a collecting vessel. Reactor and collecting vessel may be washed out with $SiX_4$.

Preferably, methane alone or, in addition to methane, other volatile compounds from the group consisting of aliphatics and/or aromatics are used. In this case, especially, in addition to methane, ethane, ethene and/or ethyne is reacted.

Instead of or in addition to alkylated halosilanes it is possible to obtain arylated halosilanes, by using aromatics instead of or in addition to alkanes. Instead of or in addition to alkylated halosilanes it is possible to obtain alkenylated halosilanes, by using alkenes instead of or in addition to alkanes. Instead of or in addition to alkylated halosilanes it is possible to obtain alkynylated halosilanes, by using alkynes instead of or in addition to alkanes.

It is preferred to prepare organohalosilanes having different organyl substituents.

Instead of $SiX_4$ it is also possible to supply $Si_2X_6$ to the plasma reactor.

Preference is given to using one or more volatile compounds from the group consisting of halosilanes, more particularly $SiF_4$, $SiCl_4$ and/or $SiBr_4$. It is also possible to react one or more volatile compounds from the group consisting of organohalosilanes, more particularly methyltrichlorosilane. The volatile compounds, preferably of the form $MeSiX_3$, can be obtained by distillation of the organohalosilanes collected in the collecting vessel.

In a further embodiment, hydrogen additionally is reacted.

In another embodiment, doubly silylated methane (carbosilane), more particularly a bis(silyl)methane $X_3Si—CH_2—SiX_3$, is prepared.

In another embodiment it is possible additionally to prepare bis(silyl)methane $H_3Si—CH_2—SiH_3$ and/or a silylorganylated and/or a silylhalogenated derivative of bis(silyl)methane.

Furthermore, it is possible for the starting mixture additionally to comprise as a reactant one or different organohalosilanes, more particularly $R_nSiX_{4-n}$, where R is selected more particularly from the group consisting of vinyl and ethynyl.

In yet another embodiment it is possible additionally to prepare one or different organosubstituted bis(silyl)methanes, more particularly $RX_2Si—CH_2—SiX_3$ and/or $(RX_2Si)_2CH_2$, where R is selected more particularly from the group encompassing vinyl and ethynyl.

The method of the invention gets around the problems identified at the outset by starting from inexpensive $SiX_4$ or corresponding organohalosilanes and methane (nontoxic) or other volatile compounds from the group consisting of alkanes, alkenes, alkynes, and aromatics. These compounds are excited by a plasma and brought to reaction, producing, among other compounds, the desired silanes $Me_2SiX_2$, $MeSiX_3$, and $(X_3Si)_2CH_2$. A further advantage is that by replacing methane by other volatile hydrocarbons it is also possible to attach other groups to the silicon.

This is also accomplished, for example, by reacting ethene or ethyne with the tetrahalosilane in the reactor, with plasma assistance, in which case it is possible to obtain vinyl- or ethynylhalosilanes and the bis(silyl)alkanes $(X_3Si)_2CH_2$, $RX_2SiCH_2SiX_3$, and $(RSiX_2)_2CH_2$ (R=vinyl, ethynyl).

Where organosubstituted halosilanes $R_nSiX_{4-n}$ (n=1-3) instead of the tetrahalosilane are brought to reaction with hydrocarbons in the plasma reactor, success is achieved in synthesizing products with a higher degree of organic substitution on the silicon atom, or in increasing the proportions of such products in the reaction mixture, starting from silicon tetrahalide.

The method for plasma-assisted organofunctionalization of $SiX_4$ or organohalosilanes traverses a plurality of steps and may be described using $SiCl_4$ as an example, with reference to the drawing, as follows:

1. through the gas inlet (1), $CH_4$ and $SiCl_4$ are passed into the reactor (5) and
2. a plasma is ignited by application of alternating electromagnetic fields under reduced pressure (0.1-100 hPa).
3. The reactor may comprise a plurality of plasma zones (2) and rest zones (3) and also cooled surfaces. The reaction gases flow through the reactor (5) toward the vacuum pump, and
4. the volatile constituents ($SiCl_4$, $MeSiCl_3$, $Me_2SiCl_2$, etc.) are retained in a collecting vessel by deep cooling (16) (e.g., at −80° C. with cryostat).
5. After a fixed time, the reaction is ended and the collected silane mixture is run off into a distillation vessel (10), where it
6. can be separated into the individual components by fractional distillation. This produces $SiCl_4$ (reactant), $MeSiCl_3$, and $Me_2SiCl_2$ as colorless liquids.
7. Additionally, in the reactor area, yellow to brownish coatings of methylated oligosilanes and polysilanes are obtained, which
8. by dissolution with $SiCl_4$ are transferred to the collecting vessel for polysilanes (13).

The method for the methylation of tetrachlorosilane is depicted in the drawing with the following reference numerals:

1. Feed port for silicon tetrachloride and methane
2. Plasma reaction zone
3. Plasma rest zone
4. Plasma electrodes
5. Plasma reaction vessel
6. Port for vacuum pump
7. Low-temperature collecting vessel
8. Condenser
9. Distillation column
10. Distillation vessel
11. Bottom drain port
12. Drain valve
13. Collecting vessel 1
14. Service valve for inert-gas blanketing or vacuum
15. Collecting vessel 2
16. Deep-cooling device

WORKING EXAMPLES

General procedure $SiCl_4$ is introduced with the reactant gas (around 10-15 l/min) through nozzles into the reactor (5), and the plasma is ignited. The $SiCl_4$/reactant gas volume ratio can be varied arbitrarily, and other inert-gas or hydrogen admixtures are possible. Reactant gases employed also include gas mixtures (e.g., methane/ethylene or methane/hydrogen) in different ratios. The $SiCl_4$/product mixture is collected at the exit from the reactor and worked up by distillation. In this distillation, the products are isolated according to their boiling points, and identified by spectroscopy. In the working examples described here, the products are largely freed from the $SiCl_4$, the formation of product being between 25% and 60% depending on conditions. The product mixture is analyzed by gas chromatography, and the identity of individual compounds is ascertained by comparison of the fragmentation patterns and the retention times with those of authentic samples.

Product formation may be understood formally, under the prevailing plasma conditions, from a combination of free-radical reactions (e.g., $SiCl4 \rightarrow Cl.+Cl_3Si.$; $CH_4 \rightarrow .CH_3+H.$; $Cl_3Si.+H. \rightarrow Cl_3SiH$; $Cl_3Si.+.Me \rightarrow Cl_3SiMe$) and carbene insertion reactions into Si—C and Si—Si bonds (e.g., $CH_4 \rightarrow CH_2+H_2$; $R_3SiCH_3+|CH_2 \rightarrow R_3SiCH_2CH_3$; $2Cl_3Si. \rightarrow Cl_3Si—SiCl_3|CH_2 \rightarrow Cl_3Si—CH_2—SiCl_3$, etc.

Explanations/def.:
Me=methyl=—$CH_3$
Vi=vinyl=—CH=$CH_2$
Et=ethyl=—$CH_2$—$CH_3$ 1. $SiCl_4$ in the presence of methane, $CH_4$: $Me(H)SiCl_2$ (3%), $MeSiCl_3$ (8%), $Me_2SiCl_2$ (5%) By admixing hydrogen ($H_2$), the fraction of $Me(H)SiCl_2$ is particularly increased: $Me(H)SiCl_2$ (18%), $MeSiCl_3$ (17%), $Me_2SiCl_2$ (12%) If the fraction of methane is significantly reduced, $Cl_3SiCH_2SiCl_3$ is formed in a fraction of more than 40%, and the fractions of $Me(H)SiCl_2 \gg MeSiCl_3 > Me_2SiCl_2$ are now significantly lower. If, instead of methane, ethane, $C_2H_6$, is used, there is an increase in the relative proportion of methyl radicals and carbenes ($.CH_3$ and $.|CH_2$) in the reaction mixture, thereby increasing the fraction of methylated products and carbosilanes: $Cl_3SiCH_2CH_3$ (2.8%), $ViSiCl_3$ (25.49%), $MeViSiCl_2$ (1.6%), $Cl_3SiCH_2SiCl_3$ (53%), $ViCl_2SiCH_2SiCl_2Me$ (17.6%), with, additionally, small amounts of $Cl_3SiH$, $Me(H)SiCl_2$, $Cl_6Si_2$ formed.

2. $SiCl_4$ in the presence of ethane, $C_2H_4$ $HSiCl_3$ (3%), $ViSiCl_3$ (29%), $Cl_3Si—C\equiv CH$ (10.6%), $Vi_2SiCl_2$ (2.4%), $ViEtSiCl_2$ (12.7%), $Cl_3SiCH_2CH_3$ (4.7%), $Cl_3SiCH_2SiCl_3$ (38%), $Cl_3SiCH_2SiCl_2Vi$ (2.6%). If only a little ethene is fed in, the primary products are chlorinated hydrocarbons, benzene, and, in terms of silanes, almost exclusively $Cl_3SiCH_2SiCl_3$ in addition to a little $ViSiCl_3$.

If further methane, $CH_4$, is added to the ethene, the following products are formed: $HSiCl_3$ (2%), $MeSiCl_3$ (1%), $Me_2SiCl_2$ (<1%), $Cl_3SiC\equiv CH$ (3.4%), $Cl_3SiCH_2CH_3$ (5.2%), $Cl_3SiCH\!=\!CH_2$ (26%), $MeViSiCl_2$ (0.6%), $EtSiCl_3$ in traces, $Cl_3SiCH_2CH\!=\!CH_2$ (26%), $Cl_3SiCH_2CH_2CH_3$ (1.5%), $Cl_2ViSi$ ($C\equiv C\!-\!CH\!=\!CH_2$) (18%), $Cl_3SiCH_2SiCl_3$ (18%).

3. By using methyltrichlorosilane, $MeSiCl_3$, instead of $SiCl_4$, the fraction of $Me_2SiCl_2$ is significantly increased in the presence of methane. Where the combination $MeSiCl_3$/ethene is used, the following products are isolated: $SiCl_4$ (6.9%), $Me_2ViSiH$ (1.2%), $ViSiCl_3$ (32.2%), $EtSiCl_3$ (6.4%), $MeViSiCl_2$ (31%), $Cl_3SiCH_2SiCl_3$ (17.2%), $MeCl_2SiCH_2SiCl_3$ (5.1%). The combination $MeSiCl_3/CH\equiv CH$ (4-5 l/min) yields the following products: $SiCl_4$ (43.4%), $ViSiCl_3$ (3.6%), $MeViSiCl_2$ (6.8%), $Cl_3SiCH_2SiCl_3$ (46.4%).

4. Alternative procedure with reduced gas flow rates (0.2 l/min each): a mixture of $CH_4$ and $SiCl_4$ (1:1) is passed into the plasma reaction vessel 5 via the port 1 under a pressure of 1-2 hPa, and a plasma is generated in the region of the plasma electrodes (4). Then methylated chloropolysilanes deposit in the plasma reaction vessel 5 and in the collecting vessel 13. The volatile chloro- and methylchlorosilanes are condensed in the vessel 7 and collected in vessel 10, while the gaseous reaction products are taken off via the port 6. Over the course of 2.5 h, 181 g of product mixture are collected in the vessel 10, and are separated via the distillation column 9 into the individual products. In this case, from the product mixture, 21.6 g of $MeSiCl_3$ and 1.8 g of $Me_2SiCl_2$ are obtained as colorless liquids. By dissolution in $SiCl_4$, the methylated chloropolysilanes are transferred from the plasma reaction vessel 5 to the collecting vessel 13, and are taken off via the bottom drain port (11).

The invention claimed is:

1. A method for the plasma-assisted synthesis of carbosilanes, the method comprising:
performing a plasma reaction including:
passing a reactant mixture through a plasma reactor comprising a plurality of plasma reaction zones separated by a plurality of rest zones, wherein the reactant mixture comprises one or more volatile organic compounds selected from the group consisting of alkanes, alkenes, alkynes and aromatics and one or more silicon containing compounds selected from $SiX_4$, $Si_2X_6$, $R_nSiX_{4-n}$, and $R_mSi_2X_{6-m}$, wherein X is F, Cl, Br, or I, n is 1 to 4, m is 1 to 6, and R is alkyl, alkenyl, alkynyl, or aryl;
igniting nonisothermal plasma in the plurality of plasma reaction zones when the reactant mixture is in the plasma reactor such that the reactant mixture passes through the nonisothermal plasma in each of the plurality of plasma reaction zones and also passes through the plurality of rest zones; and
forming carbosilanes of the general empirical formula $R^3_q SiX_{3-q} CH_2 SiR^4_r X_{3-r}$, wherein X is F, Cl, Br or I; q=0-3; r=0-3; and $R^3$ and $R^4$ are independently selected from alkyl, alkenyl, alkynyl, and aryl,
wherein the reactant mixture is reacted in the plasma reactor under a pressure of 0.1 to 100 hPa, the ratio of volatile organic compound(s) to silicon containing compound(s) is about 1:1 or less, and the plasma reaction is carried out by coupling-in alternating electromagnetic fields in the 1.0 MHz to 2.45 GHz range.

2. The method of claim 1, wherein the plasma reactor comprises a plurality of reaction zones and rest zones which follow one another alternately and the method includes passing the reactant mixture through the plurality of reaction zones and rest zones.

3. The method claim 1, wherein the reactant mixture is reacted in the plasma reactor at reaction temperatures of 80° C. to +400° C.

4. The method claim 3, wherein the carbosilanes are recovered in a collecting vessel (7) downstream of the plasma reactor by low-temperature condensation at approximately −80° C.

5. The method claim 1, wherein the carbosilanes are obtained in a distillation vessel (10) and the method further comprises:
distilling the carbosilanes in a distillation column; and
collecting individual carbosilanes in a collecting vessel.

6. The method of claim 5, wherein the plasma reactor and the collecting vessel are washed out with $SiX_4$.

7. The method of claim 5, further comprising recovering $MeSiX_3$ from the collecting vessel (15).

8. The method of claim 1, wherein the reactant mixture further comprises methane.

9. The method of claim 8, wherein the reactant mixture further comprises ethane, ethene or ethyne.

10. The method of claim 1, wherein $R_3$ and $R_4$ are selected from alkyl and aryl.

11. The method of claim 1, wherein $R_3$ and $R_4$ are selected from alkyl and alkenyl.

12. The method of claim 1, wherein $R_3$ and $R_4$ are selected from alkyl and alkynyl.

13. The method of claim 1, wherein the reactant mixture comprises halosilanes, $SiF_4$, $SiCl_4$ or $SiBr_4$.

14. The method claim 1 wherein the reactant mixture comprises organohalosilanes or methyltrichlorosilane.

15. The method of claim 1, wherein the reactant mixture further comprises hydrogen.

16. The method of claim 1, wherein the carbosilanes comprise $X_3Si\!-\!CH_2\!-\!SiX_3$.

17. The method of claim 1, wherein the carbosilanes comprise bis(silyl)methane $H_3Si\!-\!CH_2\!-\!SiH_3$, a silyl organylated bis(silyl) methane, or a silyl halogenated derivative of bis(silyl) methane.

18. The method of claim 1, wherein the reactant mixture comprises, $R_nSik_{4-n}$, where R is selected from vinyl and ethynyl.

19. The method of claim 1, wherein the carbosilanes comprise $RX_2Si\!-\!CH_2\!-\!SiX_3$ or $(RX_2Si)_2CH_2$, where R is selected from vinyl and ethynyl.

* * * * *